United States Patent
Choe et al.

[11] Patent Number: 6,090,516
[45] Date of Patent: Jul. 18, 2000

[54] POLYESTER TONER COMPOSITION FOR ELECTROPHOTOGRAPHIC IMAGING SYSTEMS

[75] Inventors: Eui-Won Choe, Randolph; Rao D. Mikkilineni, Warren; Hyun-Nam Yoon, New Providence; Marie Borzo, Basking Ridge; Kophu Chiang, Teaneck, all of N.J.

[73] Assignee: Hoechst Celanese Corporation, Warren, N.J.

[21] Appl. No.: 09/411,761

[22] Filed: Oct. 4, 1999

Related U.S. Application Data

[62] Division of application No. 08/923,394, Sep. 3, 1997, Pat. No. 6,001,980.

[51] Int. Cl.$^7$ ........................................................ G03G 9/09
[52] U.S. Cl. ............................................. 430/106; 430/109
[58] Field of Search ..................................... 430/106, 109

[56] References Cited

U.S. PATENT DOCUMENTS

| | | | |
|---|---|---|---|
| 4,778,742 | 10/1988 | Ong et al. | 430/106 |
| 5,200,290 | 4/1993 | Ong et al. | 430/115 |
| 5,958,998 | 9/1999 | Foucher et al. | 523/160 |

*Primary Examiner*—John Goodrow
*Attorney, Agent, or Firm*—Frommer Lawrence & Haug LLP; Jerome Rosenstock

[57] ABSTRACT

This invention provides a free-flowing polyester dye powder which has superior stability and transparency for application in electrophotographic imaging systems. In another embodiment this invention provides novel chromophoric diester monomers which are reacted with diol monomers to form an invention polyester dye. A present invention toner composition comprises particulate polyester dye, and one or more optional components such as a charge control agent or a surfactant.

23 Claims, No Drawings

POLYESTER TONER COMPOSITION FOR ELECTROPHOTOGRAPHIC IMAGING SYSTEMS

This is a divisional of prior application Ser. No. 08/923,394 filed Sep. 3, 1997 now U.S. Pat. No. 6,001,980.

BACKGROUND OF THE INVENTION

This invention generally relates to toner compositions and their utility in electrophotography. More specifically this invention relates to toner compositions having a polymeric polyester dye component for development of latent electrostatic charge patterns.

The formation and development of images on the surface of photoconductive materials by electrostatic means is well known. The basic electrophotographic imaging process (U.S. Pat. No. 2,297,691) involves placing a uniform electrostatic charge on a photoconductive insulating layer known as a photoconductor or photoreceptor, exposing the photoreceptor to a light and shadow image to dissipate the charge on the areas of the photoreceptor exposed to the light, and developing the resulting electrostatic latent image by depositing on the image a finely divided electroscopic toner material. The toner will normally be attracted to those areas of the photoreceptor which retain a charge, thereby forming a toner image corresponding to the electrostatic latent image. This developed image may then be transferred to a substrate such as paper. The transferred image subsequently may be permanently affixed to the substrate by heat, pressure, a combination of heat and pressure, or other suitable fixing means such as solvent or overcoating treatment.

Toner and developer compositions including colored developer compositions are in wide use. These compositions normally contain toner particles consisting of resin and colorants, and carrier particles. The colorants usually are selected from cyan dyes or pigments, magenta dyes or pigments, yellow dyes or pigments, and mixtures thereof.

One of the main advantages of selecting organic dyes instead of pigments for color toner compositions resides in the provisions of increased color fidelity as the dyes can be molecularly dispersed in the toner resins. To obtain a homogeneous dispersion, it is generally necessary to build into these molecules certain substituents for enhancing their compatibility with the toner resin. Unless the dye molecules are substantially fully compatible with the toner resins, they have a tendency to aggregate with time, especially when subjected to heat, pressure and humidity thereby resulting in a loss of color fidelity. Additionally, the low molecular weight of the dye molecules causes a high lability or mobility of the dye molecules in the toner resin resulting in undesirable bleeding of the dyes.

Of particular interest with respect to the present invention are toner compositions which include a chromophoric resin ingredient. U.S. Pat. No. 3,699,135 describes a polymer dye prepared by the copolymerization of a silane with an anthraquinone containing two aliphatic hydroxyl groups. U.S. Pat. No. 4,375,357 describes water-soluble noncrystalline polymer block colorants composed of an organic polymer backbone with pendant azo chromophoric units.

Other prior art publications which describe polymeric dyes for toner compositions include U.S. Pat. Nos. 3,553,133; 4,645,727; 4,778,742; 5,200,290; 5,212,033; 5,296,325; and 5,437,953; incorporated by reference.

There is continuing interest in the development of new and improved toner compositions for application in electrophotography.

Accordingly, it is an object of this invention to provide a polymeric dye toner composition which has a superior combination of properties for electrophotographic imaging systems.

It is another object of this invention to provide chromophoric monomers which are adapted for preparation of polyester dyes by a copolymerization reaction.

Other objects and advantages of the present invention shall become apparent from the accompanying description and examples.

DESCRIPTION OF THE INVENTION

One or more objects of the present invention are accomplished by the provision of a chromophoric monomer corresponding to the formula:

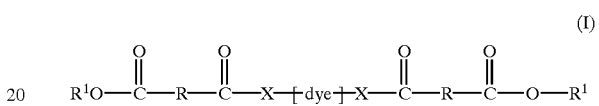

where X is —O— or —NH—; R is a covalent bond or a divalent $C_1$–$C_{16}$ aliphatic, alicyclic or aromatic radical; and $R^1$ is a $C_1$–$C_6$ aliphatic radical.

The R radical is illustrated by straight or branched-chain alkylene groups such as ethylene, 2-ethylhexylene, octylene and decylene; alicyclic groups such as cyclopentylene and cyclohexylene; aromatic groups such as phenylene, tolylene, xylylene, biphenylene, naphthylene, pyridylene, and the like.

The $R^1$ radical is illustrated by substituents such as methyl, ethyl, propyl, 2-methylpropyl, hydroxyethyl, 3-hydroxy-2-methylpropyl, and the like.

A formula I chromophoric monomer can be prepared by the following type condensation reaction:

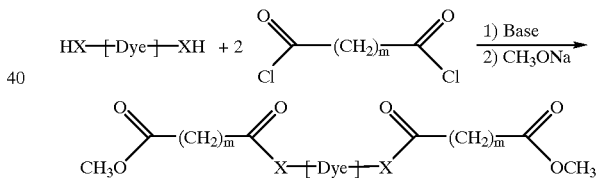

The acyl chloride can be a difunctional reactant such as malonoyl chloride, adipoyl chloride, sebacoyl chloride, isophthaloyl chloride, terephthaloyl chloride, and the like.

Illustrative of formula I chromophoric monomers are bis($C_1$–$C_6$ alkyl sebacamide) of 6'-butoxy-2,6-diamino-3,3'-azodipyridine; bis(methyl sebacamide) of 6'-butoxy-2,6-diamino-3,3'-azodipyridine; bis($C_1$–$C_6$ alkyl sebacamide) of thionine; bis(methyl sebacamide) of thionine; bis($C_1$–$C_6$ alkyl sebacamide) of basic fuchsin; bis(methyl sebacamide) of basic fuchsin; bis($C_1$–$C_6$ alkyl sebacamide) of 3,6-diaminoacridine hydrochloride; bis(methyl sebacamide) of 3,6-diaminoacridine hydrochloride; bis($C_1$–$C_6$ alkyl sebacate) of 4-(4-nitrophenylazo)resorcinol; bis(methyl sebacate) of 4-(4-nitrophenylazo)resorcinol; bis($C_1$–$C_6$ alkyl sebacamide) of 2,9-dimethylquinacridone; bis(methyl sebacamide) of 2,9-dimethylquinacridone; bis($C_1$–$C_6$ alkyl sebacamide) of 1,4-bis(ethylamino)-9,10-anthraquinone; bis (methyl sebacamide) of 1,4-bis(ethylamino)-9,10-anthraquinone; bis($C_1$–$C_6$ alkyl sebacamide) of 1,4-bis(n-butylamino)-9,10-anthraquinone; bis(methyl sebacamide) of 1,4-bis(n-butylamino-9,10-anthraquinone; bis($C_1$–$C_6$ alkyl sebacamide) of 1,4-bis(4-methylanilino)-9,10- anthraquinone; bis(methyl sebacamide) of 1,4-bis(4-methylanilino)-9,10-anthraquinone; bis($C_1$–$C_6$ alkyl sebacamide) of 2,3-dihydro-2,2-dimethyl-6-[[4-(phenylazo)-1-naphthalenyl]azo]-1H-perimidine; bis (methyl sebacamide) of 2,3-dihydro-2,2-dimethyl-6-[[4-(phenylazo)-1-naphthalenyl]azo]-1H-perimidine; and the like.

In another embodiment this invention provides a chromophoric monomer corresponding to the formula:

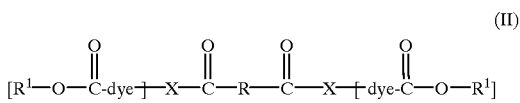

(II)

where X is —O— or —NH—; and R is a covalent bond or a divalent $C_1$–$C_{16}$ aliphatic, alicyclic or aromatic radical; and $R^1$ is a $C_1$–$C_6$ aliphatic radical.

The R and $R^1$ radicals in formula II can be similar to those illustrated for formula I monomers. A similar type of reaction can be employed for formula II monomer synthesis, such as the condensation of sebacoyl chloride and methyl eosin to produce bis(methyl eosin) sebacate.

In another embodiment this invention provides monomeric diols which can copolymerize with a formula I or formula II chromophoric monomer to form a polyester dye for toner compositions. The invention monomeric diols correspond to one of the formulas:

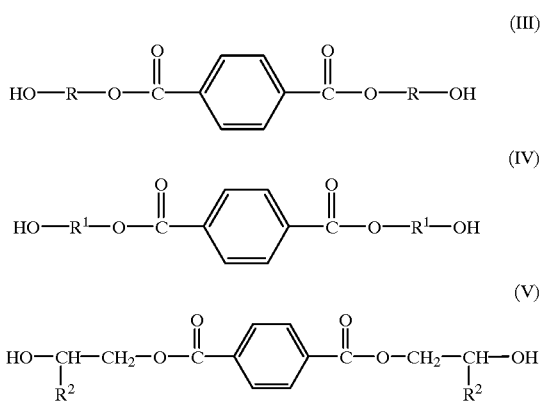

where R is normal or branched-chain $C_3$–$C_{30}$ alkylene; $R^1$ is normal or branched-chain $C_8$–$C_{30}$ alkylene; and $R^2$ is normal $C_6$–$C_{28}$ alkyl.

Illustrative of formulas III–V monomeric diols are bis(3-hydroxy-2-methylpropyl) terephthalate; bis(2-tetradecyl-2-hydroxyethyl) terephthalate; bis(2-hexyl-2-hydroxyethyl) terephthalate; and the like.

An important aspect of the present invention is the provision of a toner composition which has a superior combination of physicochemical properties for application in electrophotographic imaging systems.

A toner composition of the present invention comprises, as a main component, a polyester dye having between about 0.1–20 mole percent of recurring chromophoric diester monomer units, and having a weight average molecular weight between about 5000–100,000, and exhibiting a glass transition temperature ($T_g$) between about 40°–120° C., and a melt-viscosity between about 200–5500 poises at 150° C.

In a preferred toner composition the polyester dye has a weight average molecular weight between about 10,000–30,000, and/or the toner composition has a polydispersity between about 1.2–4, and/or exhibits a melt index between about 25–1000 grams per 10 minutes at 150° C. under a load of 2.16 kilograms, and/or exhibits at least 80% optical transparency at a specific wavelength within the range between about 350–750 nanometers.

The chromophoric entity in a present invention monomer or polyester dye is selected from organic structures which include yellow 6'-butoxy-2,6-diamino-3,3'-azodipyridine; blue thionine; red basic fuchsin; magenta; 3,6-diaminoacridine hydrochloride; red methyl eosin; yellow 4-(4-nitrophenylazo)resorcinol; magenta 2,9-dimethylquinacridine; yellow 2,2'-[(3,3'-dichloro-1,1'-diphenyl)-4,4'-bis(azo)]-bis[N-(2-methoxyphenyl)]-3-oxobutanamide; cyan 1,4-bis(ethylamino)-9,10-anthraquinone; cyan 1,4-bis(n-butylamino)-9,10-anthraquinone; cyan 1,4-bis(4-methylanilino)-9,10-anthraquinone; black 2,3-dihydro-2,2-dimethyl-6-[[(4-phenylazo)-1-naphthylenyl]-azo]-1H-perimidine; and the like. A selected chromophoric structure has the requisite difunctionality to convert to a chromophoric monomer in accordance with the present invention.

A present invention polyester dye can be prepared by solution, suspension or non-aqueous dispersion polymerization methods. Methods for the preparation of chromophoric dyes are described in publications which include U.S. Pat. No. 4,645,727 and U.S. Pat. No. 4,778,742 and citations therein; incorporated by reference.

A present invention toner composition can include between about 0.001–2 weight percent of a charge control agent for the purpose of imparting a positive charge to toner composition particles. The toner particles typically have an average particle size between about 2–20 microns.

Suitable charge control agents include carboxylated salts such as zinc heptanoate and aluminum 2-ethylhexanoate; lecithin; polyisobutylene succinimide; cetyl pyridinium chloride; and charge control agents disclosed in publications such as U.S. Pat. No. 5,200,290 and U.S. Pat. No. 5,296,325; incorporated by reference.

A present invention toner composition can include between about 0.1–10 weight percent of a surfactant ingredient to stabilize the toner composition particles. A preferred surfactant is a polymeric type as described in U.S. Pat. No. 5,200,290, such as chlorinated polypropylene and poly (ethylene-vinyl acetate).

A present invention toner composition can include between about 0.5–15 weight percent of a wax ingredient, as illustrated by beeswax, paraffin wax, montan wax, carnauba wax, microcrystalline wax, fatty alcohols, fatty esters, and the like.

A present invention toner composition also can include between about 1–30 weight percent of a particulate co-host resin such as styrene/methacrylate copolymer, styrene/butadiene copolymer, pentaerythritol terephthalate polyester, and the like, which is interspersed with the polyester dye particles.

A present invention toner composition has superior properties for purposes of electrophotographic imaging systems. A invention toner composition is a free-flowing powder which is a stable dispersion having a long shelf and storage life. Desirable print density and print quality, and excellent color quality, can be achieved in electrostatic image development with an invention toner composition.

The following examples are further illustrative of the present invention. The components and specific ingredients are presented as being typical, and various modifications can be derived in view of the foregoing disclosure within the scope of the invention.

EXAMPLE I

Bis(methyl sebacamide) of 6'-butoxy-2,6-diamino-3,3'-azodipyridine (yellow)

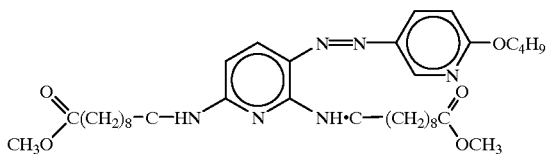

In a 500 ml three-necked flask equipped with nitrogen inlet and outlet, thermometer, condenser and mechanical stirrer, are placed 47.828 grams (0.2 m) of sebacoyl chloride and 200 grams of N-methyl-2-pyrrolidone. Sodium methoxide (10.80 grams, 0.2 m) is added into the flask. The resulting mixture is stirred at ambient temperature for 30 minutes. 6'-Butoxy-2,6-diamino-3,3'-azodipyridine (28.634 grams, 0.1 m) in 500 ml of N-methyl-2-pyrrolidone is added into the flask with fast agitation. The reaction mixture is stirred for one hour at ambient temperature, and then poured into distilled water. The solution is basified with dilute sodium hydroxide to precipitate a yellow solid. The recovered product is filtered, washed with water, and dried at 75° and 0.1 Torr to obtain 20.6 grams of yellow monomer with a melting point range of 120°–172° C. The monomer is soluble in HFIP[(1)] AT 10%, in NMP[(2)] at 5%, and soluble at 5% in hot DMSO[(3)] and hot ethanol.

[(1)]hexafluoroisopropanol.
[(2)]N-methyl-2-pyrrolidone.
[(3)]dimethylsulfoxide.

EXAMPLE II

Bis(methyl sebacamide) of thionine (blue)

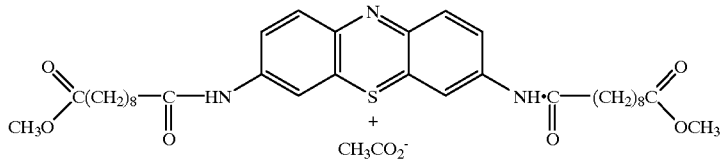

In a 500 ml three-necked flask equipped with nitrogen inlet and outlet, thermometer, condenser and mechanical stirrer, are placed 32.5 grams (0.1359 m) of sebacoyl chloride and 200 grams of N-methyl-2-pyrrolidone. Sodium methoxide (7.341 grams, 0.1359 m) is added into the flask. The resulting mixture is stirred at ambient temperature for 30 minutes. Thionine (19.525 grams, 0.068 m) in 300 ml of N-methyl-2-pyrrolidone is added into the flask with fast agitation. The reaction mixture is stirred for one hour at ambient temperature, and then poured into distilled water. The product precipitate is filtered, washed with water, and dried at 75° C. and 0.1 Torr to obtain 52.63 grams of viscous blue monomer. The monomer is soluble in HFIP and DMSO at 10%, in NMP at 5%, and partially soluble in ethanol.

EXAMPLE III

Bis(methyl sebacamide) of basic fuchsin (red)

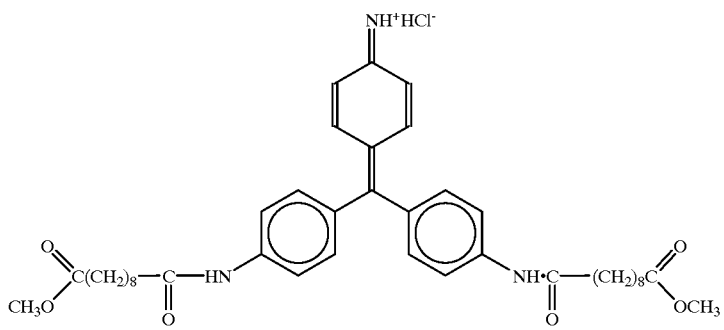

In a 500 ml three-necked flask equipped with nitrogen inlet and outlet, thermometer, condenser and mechanical stirrer, are placed 47.828 grams (0.2 m) of sebacoyl chloride and 200 grams of N-methyl-2-pyrrolidone. Sodium methoxide (10.80 grams, 0.2 m) is added into the flask. The resulting mixture is stirred at ambient temperature for 30 minutes. Basic fuchsin (32.383 grams, 0.1 m) in 500 ml of N-methyl-2-pyrrolidone is added into the flask with fast agitation. The reaction mixture is stirred for one hour at ambient temperature, and then poured into distilled water. The product precipitate is filtered, washed with water, and dried at 75° C. and 0.1 Torr to obtain 20.6 grams of red monomer with a melting point range from 75.1° to 85.3° C. The solid is soluble at 10% in HFIP, in NMP, in DMSO, and partially soluble in hot ethanol.

In a 500 ml three-necked flask equipped with nitrogen inlet and outlet, thermometer, condenser and mechanical stirrer, are placed 4.0654 grams (0.017 m) of sebacoyl chloride and 200 grams of N-methyl-2-pyrrolidone. Methyl eosin (Solvent Red 44) (23.25 grams, 0.034 m) is added into the flask. The resulting mixture is stirred for one hour at ambient temperature, and then poured into distilled water. The product precipitate is filtered, washed with water, and dried at 75° C. and 0.1 Torr to obtain 23.25 grams of red monomer with a melting point range from 232.2° to 237° C. The solid is insoluble at 10% in hot HFIP, partially soluble at 10% in NMP, soluble in hot NMP, soluble at 10% in DMSO, and insoluble in hot ethanol.

EXAMPLE IV

Bis(methyl sebacamide) of 3,6-diaminoacridine hydrochloride (magenta)

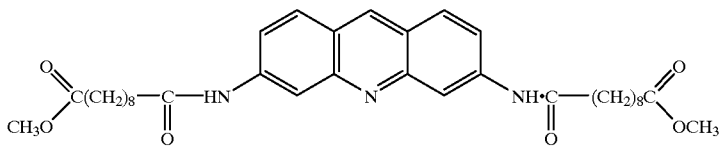

In a 500 ml three-necked flask equipped with nitrogen inlet and outlet, thermometer, condenser and mechanical stirrer, are placed 47.828 grams (0.2 m) of sebacoyl chloride and 200 grams of N-methyl-2-pyrrolidone. Sodium methoxide (10.80 grams, 0.2 m) is added into the flask. The resulting mixture is stirred at ambient temperature for 30 minutes. 3,6-Diaminoacridine HCl (24.571 grams, 0.1 m) in 500 ml of N-methyl-2-pyrrolidone is added into the flask with fast agitation. The reaction mixture is stirred for one hour at ambient temperature, and then poured into distilled water. The product precipitate is filtered, washed with water, and dried at 75° C. and 0.1 Torr to obtain 47.87 grams of magenta monomer with a melting point range from 152.1° to 171.1° C. The solid is soluble at 10% in HFIP, partially soluble at 5% in NMP or DMSO, and soluble in hot NMP or DMSO, and insoluble in hot ethanol.

EXAMPLE V

Bis(methyl eosin) sebacate (red)

EXAMPLE VI

Bis(methyl sebacate) of 4-(4-nitrophenylazo) resorcinol (yellow)

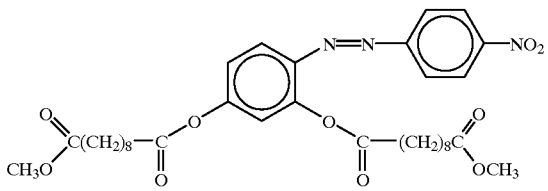

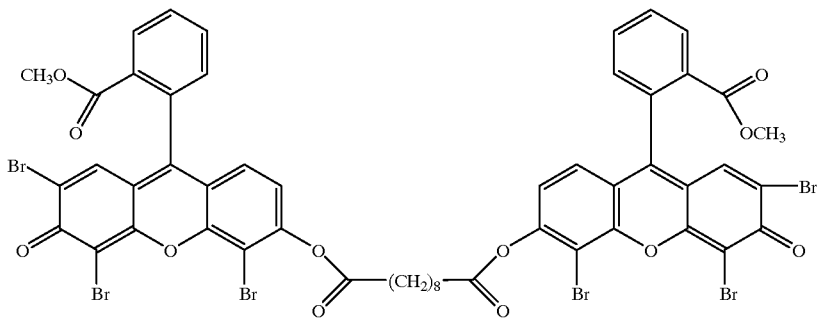

In a 500 ml three-necked flask equipped with nitrogen inlet and outlet, thermometer, condenser and mechanical stirrer, are placed 38.88 grams of 4-(4-nitrophenylazo) resorcinol (0.15 m), 24 grams of 50% NaOH solution, and 200 grams of N-methyl-2-pyrrolidone. The resulting mixture is stirred at ambient temperature for 30 minutes. To 71.742 grams (0.3 m) of sebacoyl chloride in 500 ml of N-methyl-2-pyrrolidone is added 16.21 grams of sodium methoxide (0.3 m). The resulting solution is stirred for 30 minutes, and then is added into the flask with fast agitation. The reaction mixture is stirred for one hour at ambient temperature, and then poured into distilled water. The product precipitate is filtered, washed with water, and dried at 75° C. and 0.1 Torr to obtain 47.87 grams of yellow monomer with a melting point range from 101° to 108° C. The solid is insoluble at 10% in hot HFIP, soluble at 10% in NMP or DMSO, partially soluble at 10% in ethanol, and soluble in hot ethanol.

EXAMPLE VII

Bis(methyl sebacamide) of 2,9-dimethylquinacridone (magenta)

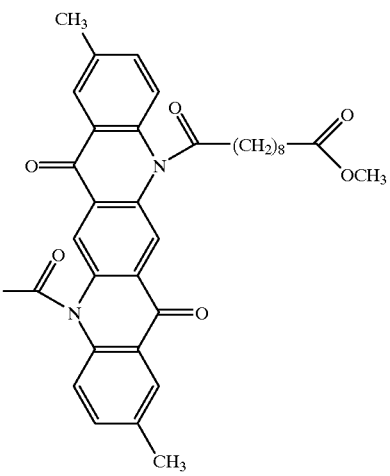

In a one liter three-necked flask equipped with nitrogen inlet and outlet, thermometer, condenser and mechanical stirrer, are placed 35.63 grams of 2,9-dimethylquinacridone (0.1046 m), and 100 grams of N-methyl-2-pyrrolidone. The resulting mixture is stirred at ambient temperature for 30 minutes. To 50 grams (0.2091 m) of sebacoyl chloride in 400 ml of N-methyl-2-pyrrolidone, is added 11.29 grams of sodium methoxide (0.2091 m). The resulting solution is stirred for 30 minutes and then added into the flask with fast agitation. The reaction mixture is stirred for one hour at ambient temperature, heated for 2 hours at 100° C., and then poured into distilled water (5 l). The product precipitate is filtered, washed with water, and dried at 75° C. and 0.1 Torr to obtain 63.2 grams of magenta monomer with a melting point range from 135° to 160° C.

Following the procedures described in Examples I–VII, corresponding dye monomers are prepared with each of adipoyl chloride, isophthaloyl chloride and terephthaloyl chloride employed in place of sebacoyl chloride.

EXAMPLE VIII

Bis(3-hydroxy-2-methylpropyl) terephthalate

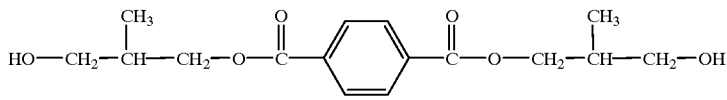

In a 2 liter three-necked flask equipped with nitrogen inlet and outlet, thermometer, condenser and mechanical stirrer, are placed 776.1 grams (4 m) of dimethyl terephthalate, 828 grams (9.2 m) of 2-methyl-1,3-propanediol and 0.6936 grams of titanium tetraisopropoxide. The mixture is heated at 210° C. for 2.5 hours while distilling out methanol. The reaction temperature is raised to 250° C., and excess 2-methyl-1,3-propanediol is distilled off. The resulting product is cooled to room temperature, and recrystallized from methanol to provide 1091 grams of terephthalate diol monomer.

In a similar manner, 1,2-propanediol is employed as the alcohol reactant to produce bis(2-hydroxypropyl) terephthalate.

EXAMPLE IX

Bis(2-tetradecyl-2-hydroxyethyl) terephthalate

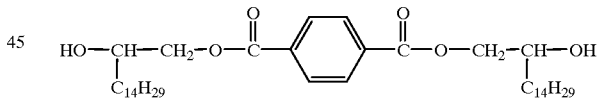

In a one liter three-necked resin flask equipped with nitrogen inlet and outlet, thermometer, condenser and mechanical stirrer, are placed 97.1 grams (0.5 m) of dimethyl terephthalate, 258.45 grams (1 m) of 1,2-hexadecanediol and 0.0865 grams of titanium tetraisopropoxide. The mixture is heated at 210° C. for 2.5 hours while distilling out methanol. The reaction temperature is raised and held at 250° C. for 0.5 hour. The resulting product is cooled to room temperature to provide a quantitative yield of terephthalate diol.

In a similar manner, 1,2-octanediol is employed as a reactant to obtain bis(2-hexyl-2-hydroxyethyl) terephthalate.

EXAMPLE X

Polyester dye of polymerized yellow bis(3-hydroxy-2-methylpropyl) terephthalate of 2,2'-[(3,3'-dichloro-1,1'-diphenyl)-4,4'-bis(azo)]-bis[N-(2-methoxyphenyl)]-3-oxobutanamide

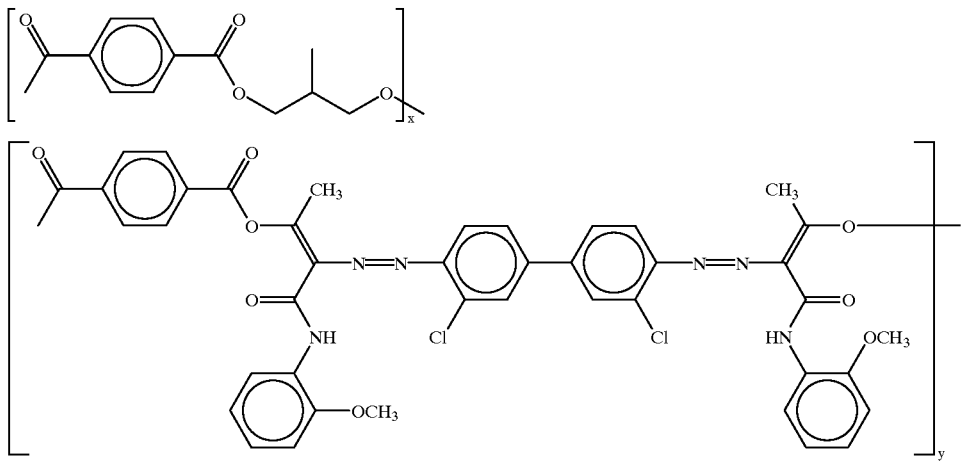

where x/y is 98.66/1.34 mole percent.

In a one liter three-necked resin flask equipped with nitrogen inlet and outlet, thermometer, condenser and mechanical stirrer, are placed 200 grams (0.604 m) of bis(3-hydroxy-2-methylpropyl) terephthalate and 6 grams of 2,2'-[(3,3'-dichloro-1,1'-diphenyl)-4,4'-bis(azo)]-bis[N-(2-methoxyphenyl)]-3-oxobutanamide (C.I. Pigment Yellow 17). The resulting mixture is heated to 210° C. under vacuum, and the polymerization temperature is maintained for 3 hours. The resulting polymer is cooled to room temperature to obtain yellow copolyester with a weight average molecular weight of 23,200 and number average molecular weight of 8400, a polydispersity of 2.8, a glass transition temperature of 49° C., a heat of fusion of 0 j/g, a softening at about 100° C., a melt-viscosity of 1220 poises at 150° C., and a melt index of 110 g/10 min. at 150° C. under a load of 2.16 Kg.

The polyester mixture is pulverized to an average particle size of about 5–7 microns suitable for electrophotographic imaging systems.

The procedure is repeated, except that the polymerization temperature is 240° C.

The polyester dye product has a weight average molecular weight of 33,000 and number average molecular weight of 10,800, a polydispersity of 3.1, a glass transition temperature of 53° C., a heat of fusion of 0 j/g, a softening at about 100° C., a melt-viscosity of 7020 poises at 150° C., and a melt index of 19 g/10 min. at 150° C. under a load of 2.16 Kg.

The polyester mixture is pulverized to an average particle size of about 5–7 microns.

EXAMPLE XI

Polyester dye of polymerized yellow bis(2-hydroxypropyl) terephthalate of 2,2'-[(3,3'-dichloro-1,1'-diphenyl)-4,4'-bis(azo)]-bis[N-(2-methoxyphenyl)]-3-oxobutanamide

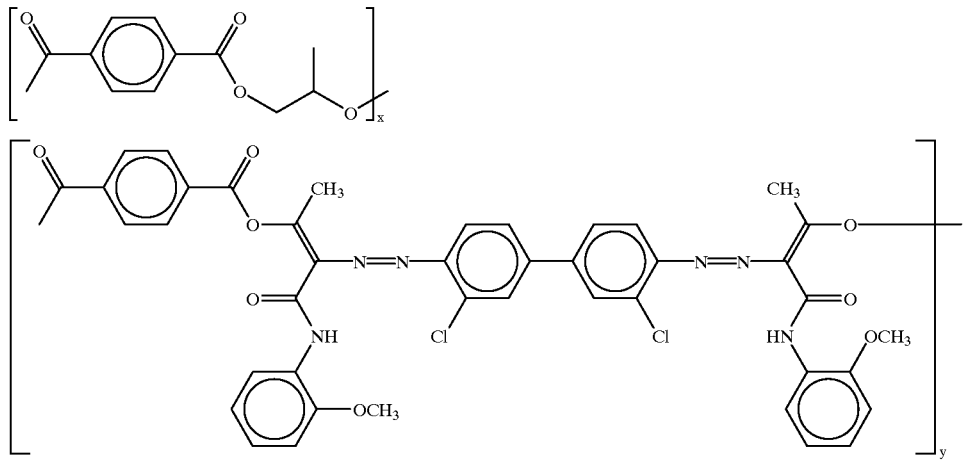

where x/y is 99.64/0.36 mole percent.

In a one liter three-necked resin flask equipped with nitrogen inlet and outlet, thermometer, condenser and mechanical stirrer, are placed 193.49 grams (0.9964 m) of dimethyl terephthalate, 175.04 grams (2.3 m) of 1,2-propanediol, and 2.48 grams (0.0036 m) of 2,2'-[3,3'-dichloro-1,1'-diphenyl)-4,4'-bis(azo)]-bis[N-(2-methoxyphenyl)]-3-oxobutanamide (C.I. Pigment Yellow 17). The resulting mixture is heated to 210° C. for 2 hours, at 240° C. for 30 minutes, and then at 210° C. for 3 hours at 1 Torr. The resulting polymer is cooled to room temperature to obtain yellow copolyester with a weight average molecular weight of 10,000 and number average molecular weight of 4600, a polydispersity of 2.1, a glass transition temperature of 75° C., a heat of fusion of 0 j/g, a softening temperature at about 130° C., a melt-viscosity of 832 poises at 150° C., and a melt index of 160 g/10 min. at 150° C. under a load of 2.16 Kg.

The copolyester is pulverized to an average particle size of 5–7 microns suitable for electrophotographic imaging systems.

EXAMPLE XII

Polyester dye of copolymerized bis(2-hydroxypropyl) terephthalate, bis(hydroxyethyl) terephthalate and yellow 2,2'-[3,3'-dichloro-1,1'-diphenyl)-4,4'-bis(azo)]-bis[N-2-methoxyphenyl)]-3-oxobutanamide where x/y/z is 39.66/60/0.35 mole percent.

In a one liter three-necked resin flask equipped with nitrogen inlet and outlet, thermometer, condenser and mechanical stirrer, are placed 169.37 grams (0.6 m) of bis(2-hydroxypropyl) terephthalate, 100.83 grams (0.3966 m) of bis(hydroxyethyl) terephthalate, 2.5 grams (0.0036 m) of 2,2'-[(3,3'-dichloro-1,1'-diphenyl]-4,4'-bis(azo)]-bis[N-(2-methoxyphenyl)]-3-oxo-butanamide (C.I. Pigment Yellow 17), and 0.07 grams of titanium tetraisopropoxide. The resulting mixture is heated to 210° C. for 30 minutes, and then vacuum is applied. The polymerization temperature is maintained at that temperature for 2 hours. The resulting polymer is cooled to room temperature to obtain yellow copolyester with a weight average molecular weight of 7300 and number average molecular weight of 3400, a polydispersity of 2.1, a glass transition temperature of 63° C., a heat of fusion of 0 j/g, a softening temperature range of 100°–130° C., a melt-viscosity of 377 poises at 150° C., and a melt index of 360 g/10 min. at 150° C. under a load of 2.16 Kg.

The copolyester is pulverized to an average particle size of 5–7 microns suitable for electrophotographic imaging systems.

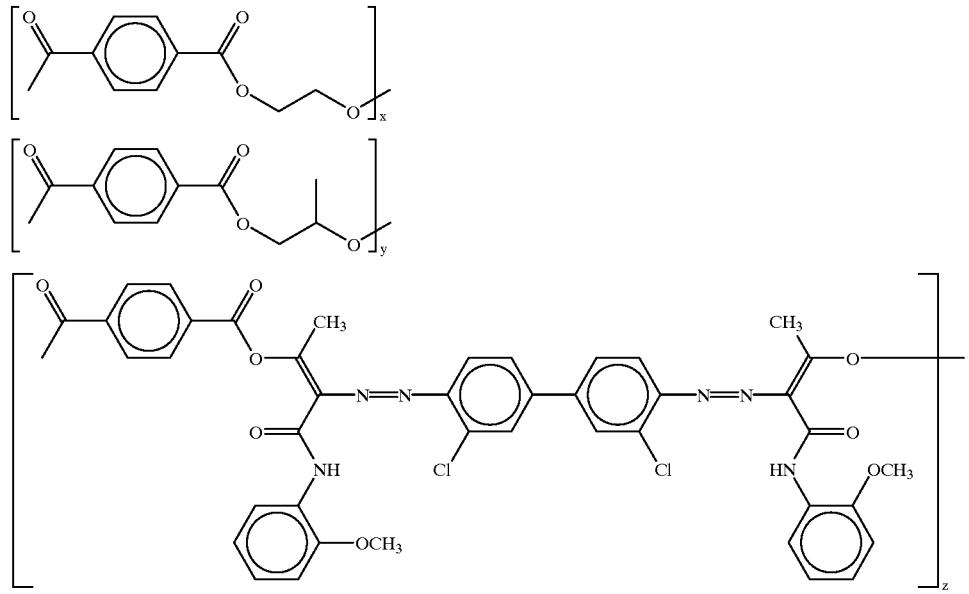

EXAMPLE XIII

Polyester dye of copolymerized bis(3-hydroxy-2-methylpropyl) terephthalate, bis(hydroxyethyl) terephthalate and yellow 2,2'-[(3,3'-dichloro-1,1'-diphenyl)-4,4'-bis(azo)]-bis[N-(2-methoxyphenyl)]-3-oxobutanamide

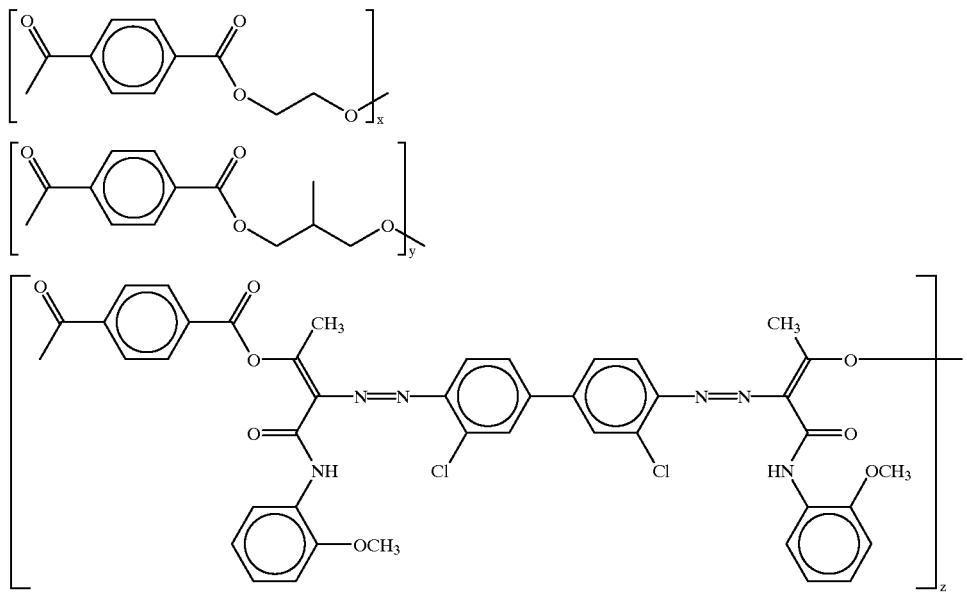

where x/y/z is 64.66/35/0.34 mole percent.

In a one liter three-necked resin flask equipped with nitrogen inlet and outlet, thermometer, condenser and mechanical stirrer, are placed 108.62 grams (0.35 m) of bis(3-hydroxy-2-methylpropyl) terephthalate, 164.39 grams (0.6466 m) of bis(hydroxyethyl) terephthalate, 2.5 grams (0.0034 m) of 2,2'-[(3,3'-dichloro-1,1-diphenyl)-4,4'-bis(azo)]-bis[N-(2-methoxyphenyl)]-3-oxo-butanamide (C.I. Pigment Yellow 17), and 0.12 grams of titanium tetraisopropoxide. The resulting mixture is heated to 210° C. for 30 minutes, and then vacuum is applied. The polymerization temperature is maintained at that temperature for 45 minutes. The resulting polymer is cooled to room temperature to obtain yellow copolyester with a weight average molecular weight of 14,000 and number average molecular weight of 6400, a polydispersity of 2.2, a glass transition temperature of 53° C., a heat of fusion of 0 j/g, a softening temperature at about 115°–120° C., a melt-viscosity of 620 poises at 150° C., and a melt index of 220 g/10 min. at 150° C. under a load of 2.16 Kg.

The above copolyester is pulverized to an average particle size of 5–7 microns suitable for electrophotographic imaging systems.

EXAMPLE XIV

Polyester dye of copolymerized bis(3-hydroxy-2-methylpropyl) terephthalate, bis(hydroxyethyl) terephthalate and yellow 2,2'-[(3,3'-dichloro-1,1'-diphenyl)-4,4'-bis(azo)]-bis[N-(2-methoxyphenyl)]-3-oxobutanamide

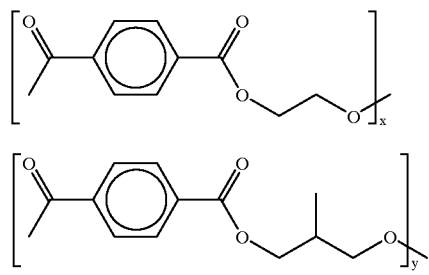

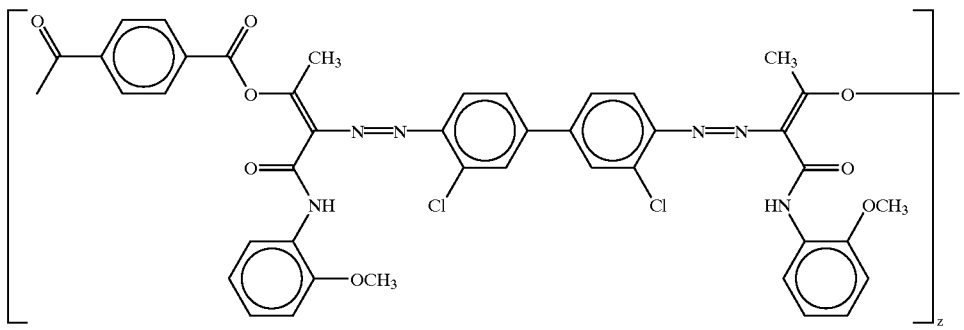

where x/y/z is 49.83/49.83/0.34 mole percent.

In a one liter three-necked resin flask equipped with nitrogen inlet and outlet, thermometer, condenser and mechanical stirrer, are placed 154.65 grams (0.4983 m) of bis(3-hydroxy-2-methylpropyl) terephthalate, 126.68 grams (0.4983 m) of bis(hydroxyethyl) terephthalate, 2.5 grams (0.0034 m) of 2,2'-[(3,3'-dichloro-1,1'-biphenyl)-4,4'-bis (azo)]-bis[N-(2-methoxyphenyl)]-3-oxo-butanamide (C.I. Pigment Yellow 17), and 0.09 grams of titanium tetraisopropoxide. The resulting mixture is heated to 210° C. for 30 minutes, and then vacuum is applied. The polymerization temperature is maintained at that temperature for one hour. The resulting polymer is cooled to room temperature to obtain yellow copolyester with a weight average molecular weight of 23,000 and number average molecular weight of 9000, a polydispersity of 2.6, a glass transition temperature of 55° C., a heat of fusion of 0 j/g, 3090 poises at 150° C., and a melt index of 44 g/10 min. at 150° C. under a load of 2.16 Kg.

The above copolyester is pulverized to an average particle size of 5–7 microns suitable for electrophotographic imaging systems.

EXAMPLE XV

Polyester dye of polymerized magenta bis(3-hydroxy-2-methylpropyl) terephthalamide of 2,9-dimethylquinacridone

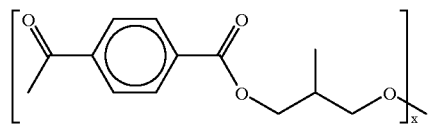

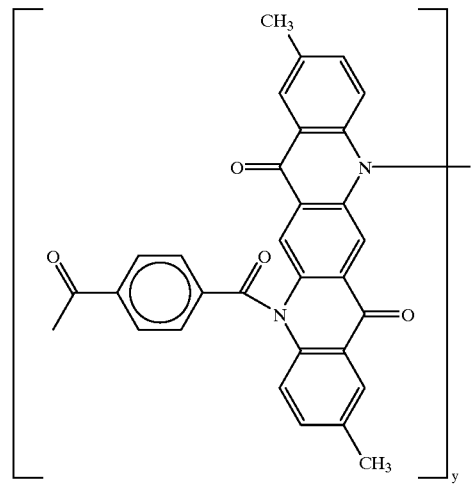

where x/y is 98.65/1.35 mole percent.

In a one liter three-necked resin flask equipped with nitrogen inlet and outlet, thermometer, condenser and mechanical stirrer, are placed 200 grams (0.6403 m) of bis(3-hydroxy-2-methylpropyl) terephthalate and 3 grams (0.088 m) of 2,9-dimethylquinacridone. The resulting mixture is heated to 225° C. under vacuum, and the polymerization temperature is maintained for 3 hours. The resulting polymer is cooled to room temperature to obtain-magenta copolyester with a weight average molecular weight of 29,800 and number average molecular weight of 10,000, a polydispersity of 3.0, a glass transition temperature of 52° C., a heat of fusion of 0 j/g, a softening at about 100° C., a melt-viscosity of 3170 poises at 150° C., and a melt index of 43 g/10 min. at 150° C. under a load of 2.16 Kg.

The polyester mixture is pulverized to an average particle size of about 5–7 microns.

EXAMPLE XVI

Polyester dye of copolymerized bis(3-hydroxy-2-methylpropyl) terephthalate, bis(hydroxyethyl) terephthalate and magenta bis(methyl sebacamide) of 2,9-dimethylquinacridone

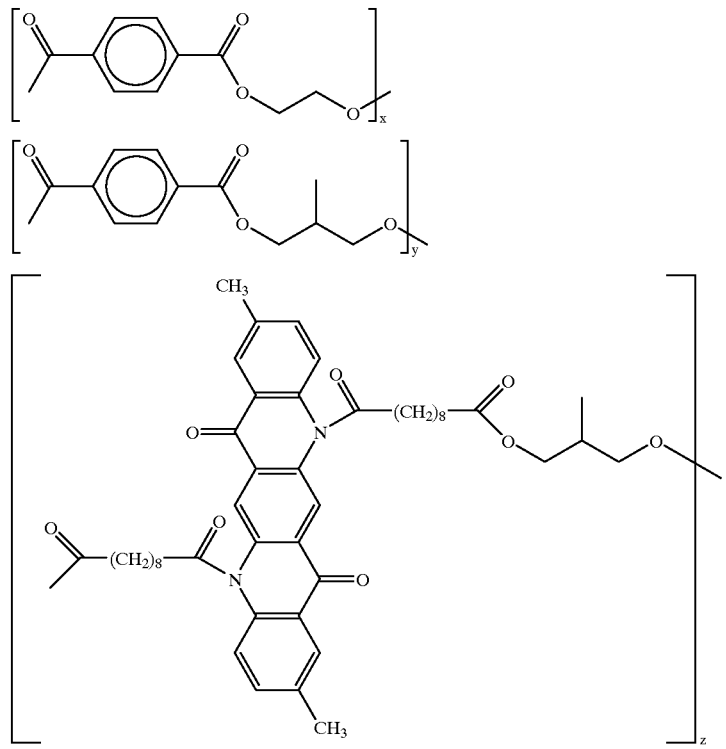

where x/y/z is 68.58/29.57/1.85 mole percent.

In a one liter three-necked resin flask equipped with nitrogen inlet and outlet, thermometer, condenser and mechanical stirrer, are placed 59.97 grams (0.1932 m) of bis(3-hydroxy-2-methylpropyl) terephthalate, 113.95 grams (0.4482 m) of bis.(hydroxyethyl) terephthalate, 8.92 grams of bis(methyl sebacamide) of 2,9-dimethylquinacridone, and 0.1021 grams of titanium tetraisopropoxide. The resulting mixture is heated to 225° C. under vacuum, and the polymerization temperature is maintained for 3 hours. The resulting polymer is cooled to room temperature to obtain magenta copolyester with a weight average molecular weight of 35,000 and number average molecular weight of 12,000, a polydispersity of 2.9, a glass transition temperature of 62° C., a heat of fusion of 0 j/g, a softening at about 145° C., a melt-viscosity of 188,000 poises at 150° C., and a melt index of 0.72 g/10 min. at 150° C. under a load of 2.16 Kg.

The copolyester mixture is pulverized to an average particle size of about 5–7 microns.

The procedure is repeated, except that x/y/z is 49.075/49.075/1.85. The copolyester has a weight average molecular weight of 46,000 and a number average molecular weight of 19,000, a polydispersity of 2.4, a glass transition temperature of 59° C., a heat of fusion of 0 j/g, a softening at about 135° C., a melt-viscosity of 8500 poises at 150° C., and a melt index of 1.6 g/10 min. at 150° C. under a load of 2.16 Kg.

EXAMPLE XVII

Polyester dye of bis(3-hydroxy-2-methylpropyl) terephthalate and magenta bis(methyl sebacamide) of 2,9-dimethylquinacridone

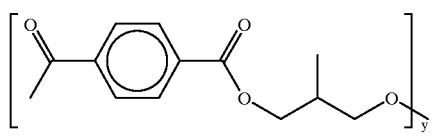

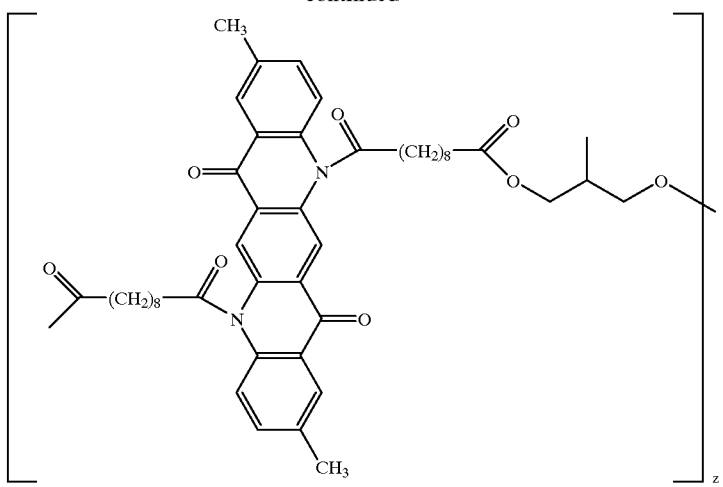

where y/z is 98.15/1.85 mole percent.

In a one liter three-necked resin flask equipped with nitrogen inlet and outlet, thermometer, condenser and mechanical stirrer, are placed 200 grams (0.64 m) of bis(3-hydroxy-2-methylpropyl) terephthalate and 8.92 grams (0.0121 m) of bis(methyl sebacamide) of 2,9-dimethylquinacridone. The resulting mixture is heated to 225° C. under vacuum, and the polymerization temperature is maintained for 3 hours. The resulting polymer is cooled to room temperature to obtain magenta copolyester with a weight average molecular weight of 20,000 and number average molecular weight 7700, a polydispersity of 2.6, a glass transition temperature of 44° C., a heat of fusion of 0 j/g, a softening at about 135° C., a melt-viscosity of 719 poises at 150° C., and a melt index of 190 g/10 min. at 150° C. under a load of 2.16 Kg.

The polyester mixture is pulverized to an average particle size of about 5–7 microns.

EXAMPLE XVIII

Polyester dye of copolymerized bis(3-hydroxy-2-methylpropyl) terephthalate, bis(hydroxyethyl) terephthalate, bis(2-tetradecyl-2-hydroxyethyl) terephthalate and magenta bis(methyl sebacamide) of 2,9-dimethylquinacridone

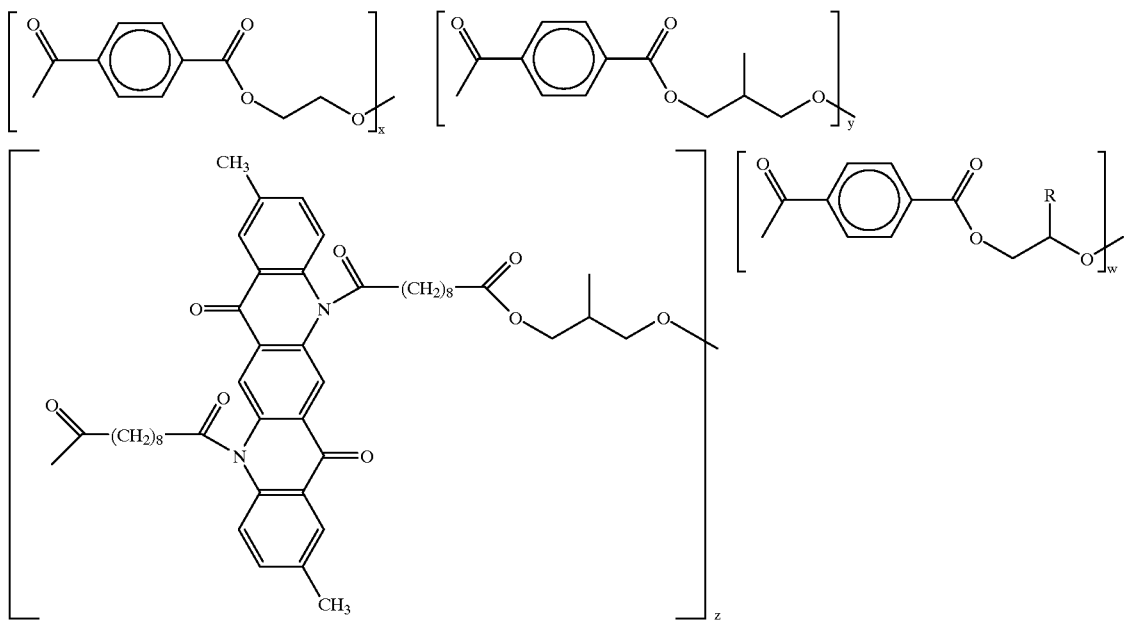

where R is $C_{14}$–$H_{29}$, and x/y/z/w is 68.18/29.22/0.8/1.8 mole percent.

In a one liter three-necked resin flask equipped with nitrogen inlet and outlet, thermometer, condenser and mechanical stirrer, are placed 59.97 grams (0.192 m) of bis(3-hydroxy-2-methylpropyl) terephthalate, 113.95 grams (0.4482 m) of bis(hydroxyethyl) terephthalate, 8.92 grams (0.0121) of bis(methyl sebacamide) of 2,9-dimethylquinacridone, 3.478 grams (0.0054 m) of bis(2-tetradecyl-2-hydroxyethyl) terephthalate, and 0.1021 grams of titanium tetraisopropoxide. The resulting mixture is heated to 225° C. under vacuum, and the polymerization temperature is maintained for 3 hours. The resulting polymer is cooled to room temperature to obtain magenta copolyester with a weight average molecular weight of 17,000 and number average molecular weight of 7600, a polydispersity of 2.2, a glass transition temperature of 52° C., a heat of fusion of 0 j/g, a softening at about 115° C., a melt-viscosity of 2280 poises at 150° C., and a melt index of 59 g/10 min. at 150° C. under a load of 2.16 Kg.

The copolyester mixture is pulverized to an average particle size of about 5–7 microns.

What is claimed is:

1. A toner composition for electrophotographic imaging systems which comprises a polyester dye having between about 0.1–20 mole percent of recurring chromophoric diester monomer units, and having a weight average molecular weight between about 5000–100,000, and exhibiting a glass transition temperature ($T_g$) between about 40°–120° C., and a melt-viscosity between about 200–5500 poises at 150° C.

2. A toner composition in accordance with claim 1 wherein the polyester dye has a weight average molecular weight between about 5,000–30,000.

3. A toner composition in accordance with claim 1 which has a polydispersity between about 1.2–4.

4. A toner composition in accordance with claim 1 which exhibits a melt index between about 25–1000 grams per 10 minutes at 150° C. under a load of 2.16 kilograms.

5. A toner composition in accordance with claim 1 which exhibits at least about 80% optical transparency at a specific wavelength within the range between about 350–750 nanometers.

6. A toner composition in accordance with claim 1 wherein the polyester dye comprises copolymerized diol monomer and yellow bis($C_1$–$C_6$ alkyl sebacamide) of 6'-butoxy-2,6-diamino-3,3'-azodipyridine monomer.

7. A toner composition in accordance with claim 1 wherein the polyester dye comprises copolymerized diol monomer and blue bis($C_1$–$C_4$ alkyl sebacamide) of thionine monomer.

8. A toner composition in accordance with claim 1 wherein the polyester dye comprises copolymerized diol monomer and red bis($C_1$–$C_6$ alkyl sebacamide) of basic fuchsin monomer.

9. A toner composition in accordance with claim 1 wherein the polyester dye comprises copolymerized diol monomer and magenta bis($C_1$–$C_6$ alkyl sebacamide) of 3,6-diaminoacridine hydrochloride monomer.

10. A toner composition in accordance with claim 1 wherein the polyester dye comprises copolymerized diol monomer and red bis(methyl eosin) sebacate.

11. A toner composition in accordance with claim 1 wherein the polyester dye comprises copolymerized diol monomer and yellow bis($C_1$–$C_6$ alkyl sebacate) of 4-(4-nitrophenylazo)resorcinol monomer.

12. A toner composition in accordance with claim 1 wherein the polyester dye comprises copolymer diol monomer and magenta bis($C_1$–$C_6$ alkyl sebacamide) of 2,9-dimethylquinacridone monomer.

13. A toner composition in accordance with claim 1 wherein the polyester dye comprises polymerized yellow bis(3-hydroxy-2-methylpropyl) terephthalate of 2,2'-[(3,3'-dichloro-1,1'-diphenyl)-4,4'-bis(azo)]-bis[N-(2-methoxyphenyl)]-3-oxobutanamide.

14. A toner composition in accordance with claim 1 wherein the polyester dye comprises copolymerized diol monomer and cyan bis($C_1$–$C_6$ alkyl sabacamide) of 1,4-bis-(ethylamino)-9,10-anthraquinone.

15. A toner composition in accordance with claim 1 wherein the polyester dye comprises copolymerized diol monomer and cyan bis($C_1$–$C_6$ alkyl sabacamide) of 1,4-bis-(n-butylamino)-9,10-anthraquinone.

16. A toner composition in accordance with claim 1 wherein the polyester dye comprises copolymerized diol monomer and cyan bis($C_1$–$C_6$ alkyl sabacamide) of 1,4-bis-(4-methylanilino)-9,10-anthraquinone.

17. A toner composition in accordance with claim 1 wherein the polyester dye comprises copolymerized diol monomer and black bis($C_1$–$C_6$ alkyl sabacamide) of 2,3-dihydro-2,2-dimethyl-6-[[4-(phenylazo)-1-naphthalenyl]azo]-1H-perimidine.

18. A toner composition in accordance with claim 1 wherein the polyester dye comprises copolymerized chromophoric diester monomer and terephthalate diol monomer corresponding to the formula:

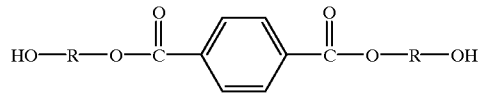

where R is normal or branched-chain $C_3$–$C_{30}$ alkylene.

19. A toner composition in accordance with claim 1 wherein the polyester dye comprises polymerized magenta bis(3-hydroxy-2-methylpropyl) terephthalamide of 2,9-dimethylquinacridone.

20. A toner composition in accordance with claim 1 which includes a liquid developer medium as an additional component.

21. A toner composition in accordance with claim 1 which includes a charge control agent as an additional component.

22. A toner composition in accordance with claim 1 which includes a surfactant as an additional component.

23. A toner composition in accordance with claim 1 which includes a wax ingredient as an additional component.

* * * * *